United States Patent [19]
Baltz et al.

[11] Patent Number: 5,821,100
[45] Date of Patent: Oct. 13, 1998

[54] **GLYCOSYLTRANSFERASE GENE GTFB FROM *AMYCOLATOPSIS ORIENTALIS***

[75] Inventors: Richard H. Baltz; Patricia J. Solenberg, both of Indianapolis, Ind.

[73] Assignee: Eli Lilly and Company, Indianapolis, Ind.

[21] Appl. No.: 926,327

[22] Filed: Sep. 5, 1997

Related U.S. Application Data

[60] Provisional application No. 60/026,027 Sep. 13, 1996.
[51] Int. Cl.$^6$ .............................. C12N 9/10; C12N 15/00; C12N 1/20; C07H 21/04
[52] U.S. Cl. ................. 435/193; 435/320.1; 435/252.3; 435/254.11; 435/325; 536/23.2
[58] Field of Search ................................ 435/193, 320.1, 435/325, 252.3, 254.11; 536/23.2

[56] References Cited

PUBLICATIONS

S. K. Chung, et al. "Biosynthetic Studies f Aricidin Antibiotics: Microbial Transformations and Glycosylations by Protoplasts." *Journal of Antibiotics* 39(5):652–659 (May 1986).

M. J. Zmijewski, Jr., and B. Briggs. "Biosynthesis of vancomycin: identification of TDP–glucose: aglycosyl–vancomycin glucosyltransferase from *Amycolatopsis orientalis.*" *FEMS Microbiology Letters* 5:129–134 (1989).

M. J. Zmijewski, Jr., and J. T. Fayerman. *Genetic and Biochemistry of Antibiotic Production* Ed. L.C. Vining and C. Stuttard. Butterworth Heinemann, Boston. Chapter 18: "Glycopeptide Antibiotics." pp. 71–83 (1995).

*Primary Examiner*—Rebecca E. Prouty
*Assistant Examiner*—Lisa J. Hobbs
*Attorney, Agent, or Firm*—Thomas D. Webster; David E. Boone

[57] ABSTRACT

The invention provides isolated nucleic acid compounds encoding the glycosyltransferase protein GtfB of *Amycolatopsis orientalis*. Also provided are vectors carrying the gtfB gene, transformed heterologous host cells for expressing the GtfB protein, and methods for producing glycopeptide compounds using the cloned gtfB gene.

10 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1221 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1221

( x i ) SEQUENCE DESCRIPTION: SEQ ID NO:1:

```
ATG  CGT  GTG  CTG  TTG  GCG  ACG  TGT  GGA  TCG  CGC  GGA  GAT  ACC  GAA  CCG      48
Met  Arg  Val  Leu  Leu  Ala  Thr  Cys  Gly  Ser  Arg  Gly  Asp  Thr  Glu  Pro
 1              5                        10                       15

CTG  GTG  GCA  CTG  GCG  GTT  CGG  GTG  CGG  GAC  CTC  GGC  GCG  GAT  GTG  CGG      96
Leu  Val  Ala  Leu  Ala  Val  Arg  Val  Arg  Asp  Leu  Gly  Ala  Asp  Val  Arg
```

-continued

|     |     |     |     | 20  |     |     |     |     | 25  |     |     |     |     | 30  |     |      |
|-----|-----|-----|-----|-----|-----|-----|-----|-----|-----|-----|-----|-----|-----|-----|-----|------|
| ATG | TGC | GCA | CCG | CCG | GAC | TGC | GCG | GAG | CGG | CTG | GCC | GAG | GTA | GGT | GTG | 144  |
| Met | Cys | Ala | Pro | Pro | Asp | Cys | Ala | Glu | Arg | Leu | Ala | Glu | Val | Gly | Val |      |
|     |     | 35  |     |     |     |     | 40  |     |     |     |     | 45  |     |     |     |      |
| CCG | CAT | GTG | CCC | GTC | GGC | CCG | TCG | GCG | CGC | GCG | CCG | ATC | CAG | CGA | GCG | 192  |
| Pro | His | Val | Pro | Val | Gly | Pro | Ser | Ala | Arg | Ala | Pro | Ile | Gln | Arg | Ala |      |
|     |     | 50  |     |     |     | 55  |     |     |     |     | 60  |     |     |     |     |      |
| AAA | CCG | TTG | ACG | GCC | GAG | GAC | GTG | CGC | CGG | TTC | ACG | ACC | GAG | GCG | ATC | 240  |
| Lys | Pro | Leu | Thr | Ala | Glu | Asp | Val | Arg | Arg | Phe | Thr | Thr | Glu | Ala | Ile |      |
| 65  |     |     |     |     | 70  |     |     |     |     | 75  |     |     |     |     | 80  |      |
| GCT | ACG | CAG | TTC | GAC | GAG | ATC | CCG | GCG | GCG | GCC | GAG | GGG | TGT | GCC | GCG | 288  |
| Ala | Thr | Gln | Phe | Asp | Glu | Ile | Pro | Ala | Ala | Ala | Glu | Gly | Cys | Ala | Ala |      |
|     |     |     |     | 85  |     |     |     |     | 90  |     |     |     |     | 95  |     |      |
| GTG | GTG | ACC | ACC | GGC | CTG | CTG | GCC | GCC | GCG | ATC | GGC | GTG | CGG | TCG | GTG | 336  |
| Val | Val | Thr | Thr | Gly | Leu | Leu | Ala | Ala | Ala | Ile | Gly | Val | Arg | Ser | Val |      |
|     |     |     | 100 |     |     |     |     | 105 |     |     |     |     | 110 |     |     |      |
| GCC | GAG | AAG | CTG | GGC | ATC | CCC | TAC | TTC | TAT | GCC | TTC | CAC | TGT | CCG | AGT | 384  |
| Ala | Glu | Lys | Leu | Gly | Ile | Pro | Tyr | Phe | Tyr | Ala | Phe | His | Cys | Pro | Ser |      |
|     |     |     | 115 |     |     |     |     | 120 |     |     |     |     | 125 |     |     |      |
| TAT | GTG | CCG | TCG | CCG | TAC | TAT | CCG | CCG | CCG | CCC | CTC | GGC | GAA | CCG | TCC | 432  |
| Tyr | Val | Pro | Ser | Pro | Tyr | Tyr | Pro | Pro | Pro | Pro | Leu | Gly | Glu | Pro | Ser |      |
|     | 130 |     |     |     |     | 135 |     |     |     |     | 140 |     |     |     |     |      |
| ACA | CAG | GAC | ACG | ATC | GAC | ATT | CCG | GCG | CAG | TGG | GAG | CGG | AAC | AAC | CAG | 480  |
| Thr | Gln | Asp | Thr | Ile | Asp | Ile | Pro | Ala | Gln | Trp | Glu | Arg | Asn | Asn | Gln |      |
| 145 |     |     |     |     | 150 |     |     |     |     | 155 |     |     |     |     | 160 |      |
| AGC | GCC | TAC | CAG | CGG | TAC | GGC | GGC | CTG | CTC | AAC | AGC | CAC | CGG | GAC | GCG | 528  |
| Ser | Ala | Tyr | Gln | Arg | Tyr | Gly | Gly | Leu | Leu | Asn | Ser | His | Arg | Asp | Ala |      |
|     |     |     |     | 165 |     |     |     |     | 170 |     |     |     |     | 175 |     |      |
| ATC | GGC | CTG | CCA | CCG | GTG | GAG | GAC | ATC | TTC | ACC | TTC | GGC | TAC | ACC | GAT | 576  |
| Ile | Gly | Leu | Pro | Pro | Val | Glu | Asp | Ile | Phe | Thr | Phe | Gly | Tyr | Thr | Asp |      |
|     |     |     | 180 |     |     |     |     | 185 |     |     |     |     | 190 |     |     |      |
| CAC | CCC | TGG | GTG | GCG | GCG | GAT | CCG | GTG | CTG | GCC | CCG | CTG | CAG | CCG | ACA | 624  |
| His | Pro | Trp | Val | Ala | Ala | Asp | Pro | Val | Leu | Ala | Pro | Leu | Gln | Pro | Thr |      |
|     |     | 195 |     |     |     |     | 200 |     |     |     |     | 205 |     |     |     |      |
| GAC | CTC | GAC | GCC | GTG | CAG | ACC | GGC | GCG | TGG | ATC | CTG | CCC | GAC | GAA | CGG | 672  |
| Asp | Leu | Asp | Ala | Val | Gln | Thr | Gly | Ala | Trp | Ile | Leu | Pro | Asp | Glu | Arg |      |
| 210 |     |     |     |     | 215 |     |     |     |     | 220 |     |     |     |     |     |      |
| CCG | CTT | TCC | CCG | GAG | CTG | GCG | GCG | TTT | CTG | GAC | GCC | GGC | CCA | CCG | CCG | 720  |
| Pro | Leu | Ser | Pro | Glu | Leu | Ala | Ala | Phe | Leu | Asp | Ala | Gly | Pro | Pro | Pro |      |
| 225 |     |     |     |     | 230 |     |     |     |     | 235 |     |     |     |     | 240 |      |
| GTG | TAC | CTG | GGG | TTC | GGC | AGC | CTG | GGC | GCA | CCT | GCT | GAC | GCG | GTC | CGG | 768  |
| Val | Tyr | Leu | Gly | Phe | Gly | Ser | Leu | Gly | Ala | Pro | Ala | Asp | Ala | Val | Arg |      |
|     |     |     |     | 245 |     |     |     |     | 250 |     |     |     |     | 255 |     |      |
| GTG | GCC | ATC | GAC | GCG | ATC | CGT | GCC | CAT | GGC | CGC | GGG | GTG | ATC | CTT | TCC | 816  |
| Val | Ala | Ile | Asp | Ala | Ile | Arg | Ala | His | Gly | Arg | Arg | Val | Ile | Leu | Ser |      |
|     |     |     | 260 |     |     |     |     | 265 |     |     |     |     | 270 |     |     |      |
| CGT | GGC | TGG | GCC | GAT | TTG | GTC | CTG | CCC | GAC | GAC | GGT | GCC | GAC | TGC | TTC | 864  |
| Arg | Gly | Trp | Ala | Asp | Leu | Val | Leu | Pro | Asp | Asp | Gly | Ala | Asp | Cys | Phe |      |
|     |     | 275 |     |     |     |     | 280 |     |     |     |     | 285 |     |     |     |      |
| GCG | ATC | GGC | GAA | GTG | AAC | CAT | CAG | GTG | CTG | TTC | GGC | CGA | GTC | GCC | GCC | 912  |
| Ala | Ile | Gly | Glu | Val | Asn | His | Gln | Val | Leu | Phe | Gly | Arg | Val | Ala | Ala |      |
|     | 290 |     |     |     |     | 295 |     |     |     |     | 300 |     |     |     |     |      |
| GTC | ATC | CAC | CAC | GGC | GGC | GCG | GGC | ACG | ACG | CAC | GTG | GCC | GCG | CGG | GCA | 960  |
| Val | Ile | His | His | Gly | Gly | Ala | Gly | Thr | Thr | His | Val | Ala | Ala | Arg | Ala |      |
| 305 |     |     |     |     | 310 |     |     |     |     | 315 |     |     |     |     | 320 |      |
| GGT | GCA | CCC | CAG | ATC | CTG | TTG | CCC | CAG | ATG | GCG | GAC | CAG | CCG | TAC | TAC | 1008 |
| Gly | Ala | Pro | Gln | Ile | Leu | Leu | Pro | Gln | Met | Ala | Asp | Gln | Pro | Tyr | Tyr |      |
|     |     |     |     | 325 |     |     |     |     | 330 |     |     |     |     | 335 |     |      |
| GCC | GGC | CGG | GTG | GCC | GAA | CTG | GGT | GTT | GGT | GTG | GCA | CAT | GAT | GGT | CCA | 1056 |
| Ala | Gly | Arg | Val | Ala | Glu | Leu | Gly | Val | Gly | Val | Ala | His | Asp | Gly | Pro |      |

|     |     |     |     |     |     |     |     | 340 |     |     |     |     |     | 345 |     |     |     |     |     | 350 |     |     |      |
|-----|-----|-----|-----|-----|-----|-----|-----|-----|-----|-----|-----|-----|-----|-----|-----|-----|-----|-----|-----|-----|-----|-----|------|

```
ATT  CCG  ACC  TTC  GAT  TCC  TTG  TCG  GCC  GCG  CTT  GCC  ACG  GCT  CTG  ACC        1104
Ile  Pro  Thr  Phe  Asp  Ser  Leu  Ser  Ala  Ala  Leu  Ala  Thr  Ala  Leu  Thr
          355                      360                     365

CCC  GAA  ACC  CAC  GCG  CGA  GCG  ACG  GCC  GTG  GCA  GGC  ACG  ATC  CGC  ACC        1152
Pro  Glu  Thr  His  Ala  Arg  Ala  Thr  Ala  Val  Ala  Gly  Thr  Ile  Arg  Thr
          370                      375                     380

GAC  GGG  GCA  GCG  GTG  GCC  GCG  CGG  TTG  CTG  CTC  GAC  GCG  GTC  AGT  CGG        1200
Asp  Gly  Ala  Ala  Val  Ala  Ala  Arg  Leu  Leu  Leu  Asp  Ala  Val  Ser  Arg
385                      390                     395                      400

GAA  AAG  CCG  ACT  GTT  TCC  GCG                                                     1221
Glu  Lys  Pro  Thr  Val  Ser  Ala
                         405
```

(2) INFORMATION FOR SEQ ID NO:2:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Arg  Val  Leu  Leu  Ala  Thr  Cys  Gly  Ser  Arg  Gly  Asp  Thr  Glu  Pro
 1              5                       10                      15

Leu  Val  Ala  Leu  Ala  Val  Arg  Val  Arg  Asp  Leu  Gly  Ala  Asp  Val  Arg
               20                       25                      30

Met  Cys  Ala  Pro  Pro  Asp  Cys  Ala  Glu  Arg  Leu  Ala  Glu  Val  Gly  Val
               35                       40                      45

Pro  His  Val  Pro  Val  Gly  Pro  Ser  Ala  Arg  Ala  Pro  Ile  Gln  Arg  Ala
     50                       55                       60

Lys  Pro  Leu  Thr  Ala  Glu  Asp  Val  Arg  Arg  Phe  Thr  Thr  Glu  Ala  Ile
 65                      70                       75                       80

Ala  Thr  Gln  Phe  Asp  Glu  Ile  Pro  Ala  Ala  Ala  Glu  Gly  Cys  Ala  Ala
                         85                       90                       95

Val  Val  Thr  Thr  Gly  Leu  Leu  Ala  Ala  Ala  Ile  Gly  Val  Arg  Ser  Val
               100                      105                     110

Ala  Glu  Lys  Leu  Gly  Ile  Pro  Tyr  Phe  Tyr  Ala  Phe  His  Cys  Pro  Ser
          115                      120                     125

Tyr  Val  Pro  Ser  Pro  Tyr  Tyr  Pro  Pro  Pro  Leu  Gly  Glu  Pro  Ser
     130                      135                      140

Thr  Gln  Asp  Thr  Ile  Asp  Ile  Pro  Ala  Gln  Trp  Glu  Arg  Asn  Asn  Gln
145                      150                      155                      160

Ser  Ala  Tyr  Gln  Arg  Tyr  Gly  Gly  Leu  Leu  Asn  Ser  His  Arg  Asp  Ala
                    165                      170                     175

Ile  Gly  Leu  Pro  Pro  Val  Glu  Asp  Ile  Phe  Thr  Phe  Gly  Tyr  Thr  Asp
               180                      185                     190

His  Pro  Trp  Val  Ala  Ala  Asp  Pro  Val  Leu  Ala  Pro  Leu  Gln  Pro  Thr
          195                      200                     205

Asp  Leu  Asp  Ala  Val  Gln  Thr  Gly  Ala  Trp  Ile  Leu  Pro  Asp  Glu  Arg
     210                      215                      220

Pro  Leu  Ser  Pro  Glu  Leu  Ala  Ala  Phe  Leu  Asp  Ala  Gly  Pro  Pro  Pro
225                      230                      235                      240

Val  Tyr  Leu  Gly  Phe  Gly  Ser  Leu  Gly  Ala  Pro  Ala  Asp  Ala  Val  Arg
                    245                      250                     255

Val  Ala  Ile  Asp  Ala  Ile  Arg  Ala  His  Gly  Arg  Arg  Val  Ile  Leu  Ser
               260                      265                     270
```

| | | | | | | | | | | | | | | |
|---|---|---|---|---|---|---|---|---|---|---|---|---|---|---|
| Arg | Gly | Trp | Ala | Asp | Leu | Val | Leu | Pro | Asp | Asp | Gly | Ala | Asp | Cys | Phe |
| | 275 | | | | | | 280 | | | | 285 | | | | |
| Ala | Ile | Gly | Glu | Val | Asn | His | Gln | Val | Leu | Phe | Gly | Arg | Val | Ala | Ala |
| | 290 | | | | | 295 | | | | | 300 | | | | |
| Val | Ile | His | His | Gly | Gly | Ala | Gly | Thr | Thr | His | Val | Ala | Ala | Arg | Ala |
| 305 | | | | | 310 | | | | | 315 | | | | | 320 |
| Gly | Ala | Pro | Gln | Ile | Leu | Leu | Pro | Gln | Met | Ala | Asp | Gln | Pro | Tyr | Tyr |
| | | | | 325 | | | | | 330 | | | | | 335 | |
| Ala | Gly | Arg | Val | Ala | Glu | Leu | Gly | Val | Gly | Val | Ala | His | Asp | Gly | Pro |
| | | | 340 | | | | | 345 | | | | | 350 | | |
| Ile | Pro | Thr | Phe | Asp | Ser | Leu | Ser | Ala | Ala | Leu | Ala | Thr | Ala | Leu | Thr |
| | | 355 | | | | | 360 | | | | | 365 | | | |
| Pro | Glu | Thr | His | Ala | Arg | Ala | Thr | Ala | Val | Ala | Gly | Thr | Ile | Arg | Thr |
| | 370 | | | | | 375 | | | | | 380 | | | | |
| Asp | Gly | Ala | Ala | Val | Ala | Ala | Arg | Leu | Leu | Leu | Asp | Ala | Val | Ser | Arg |
| 385 | | | | | 390 | | | | | 395 | | | | | 400 |
| Glu | Lys | Pro | Thr | Val | Ser | Ala | | | | | | | | | |
| | | | | 405 | | | | | | | | | | | |

( 2 ) INFORMATION FOR SEQ ID NO:3:

( i ) SEQUENCE CHARACTERISTICS:
        ( A ) LENGTH: 1221 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

```
AUGCGUGUGC UGUUGGCGAC GUGUGGAUCG CGCGGAGAUA CCGAACCGCU GGUGGCACUG      60
GCGGUUCGGG UGCGGGACCU CGGCGCGGAU GUGCGGAUGU GCGCACCGCC GGACUGCGCG     120
GAGCGGCUGG CCGAGGUAGG UGUGCCGCAU GUGCCCGUCG GCCCGUCGGC GCGCGCGCCG     180
AUCCAGCGAG CGAAACCGUU GACGGCCGAG GACGUGCGCC GGUUCACGAC CGAGGCGAUC     240
GCUACGCAGU UCGACGAGAU CCCGGCGGCG GCCGAGGGGU GUGCCGCGGU GGUGACCACC     300
GGCCUGCUGG CCGCCGCGAU CGGCGUGCGG UCGGUGGCCG AGAAGCUGGG CAUCCCCUAC     360
UUCUAUGCCU UCCACUGUCC GAGUUAUGUG CCGUCGCCGU ACUAUCCGCC GCCGCCCCUC     420
GGCGAACCGU CCACACAGGA CACGAUCGAC AUUCCGGCGC AGUGGGAGCG AACAACCAG      480
AGCGCCUACC AGCGGUACGG CGGCCUGCUC AACAGCCACC GGGACGCGAU CGGCCUGCCA     540
CCGGUGGAGG ACAUCUUCAC CUUCGGCUAC ACCGAUCACC CCUGGGUGGC GGCGGAUCCG     600
GUGCUGGCCC CGCUGCAGCC GACAGACCUC GACGCCGUGC AGACCGGCGC GUGGAUCCUG     660
CCCGACGAAC GGCCGCUUUC CCCGGAGCUG GCGGCGUUUC UGGACGCCGG CCCACCGCCG     720
GUGUACCUGG GGUUCGGCAG CCUGGGCGCA CCUGCUGACG CGGUCCGGGU GGCCAUCGAC     780
GCGAUCCGUG CCCAUGGCCG CCGGGUGAUC CUUUCCCGUG GCUGGGCCGA UUUGGUCCUG     840
CCCGACGACG GUGCCGACUG CUUCGCGAUC GGCGAAGUGA ACCAUCAGGU GCUGUUCGGC     900
CGAGUCGCCG CCGUCAUCCA CCACGGCGGC GCGGGCACGA CGCACGUGGC CGCGCGGGCA     960
GGUGCACCCC AGAUCCUGUU GCCCCAGAUG GCGGACCAGC CGUACUACGC CGGCCGGGUG    1020
GCCGAACUGG GUGUUGGUGU GGCACAUGAU GGUCCAAUUC CGACCUUCGA UUCCUUGUCG    1080
```

```
GCCGCGCUUG  CCACGGCUCU  GACCCCCGAA  ACCCACGCGC  GAGCGACGGC  CGUGGCAGGC    1140

ACGAUCCGCA  CCGACGGGGC  AGCGGUGGCC  GCGCGGUUGC  UGCUCGACGC  GGUCAGUCGG    1200

GAAAAGCCGA  CUGUUUCCGC  G                                                 1221
```

GLYCOSYLTRANSFERASE GENE GTFB FROM *AMYCOLATOPSIS ORIENTALIS*

This application claims the benefit under Title 35, United States Code, §119(e) of United States provisional patent 60/026,027 filed Sep. 13, 1996.

BACKGROUND OF THE INVENTION

This invention relates to recombinant DNA technology. In particular the invention pertains to the cloning of glycosyltransferase gene gtfB from *Amycolatopsis orientalis,* the use of the cloned gene to express and purify the encoded enzyme, and the use of the cloned enzyme for in vitro production of glycopeptide compounds.

The use of antibiotic compounds has had a profound impact on the practice of medicine in the United States and around the world. Two highly effective antibiotic compounds of the glycopeptide class, vancomycin and teichoplanin, have been approved for use in humans.

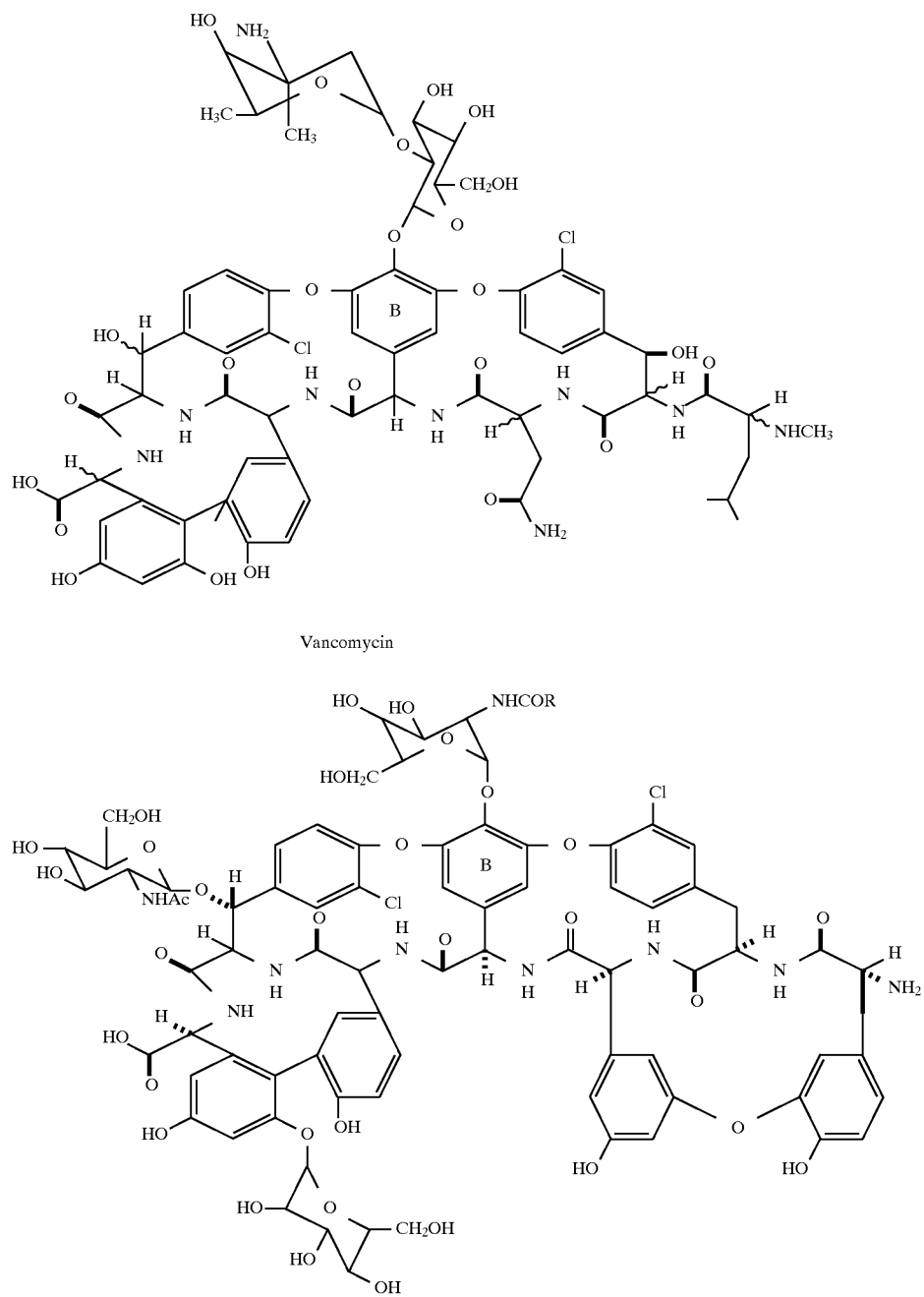

Vancomycin

Teicoplanin: R =

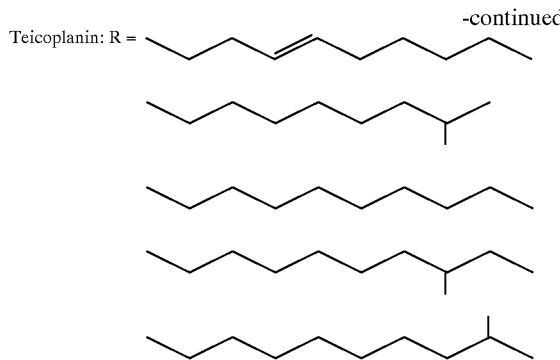

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including Streptomyces, Actinoplanes, Nocardia, Amycolatopsis, Kibdelosporangia, and Pseudonocardia. M. Zmijewski and J. Fayerman. "Glycopeptide Antibiotics," In *Genetics and Biochemistry of Antibiotic Production*, Chap. 18. Ed. L. C. Vining and C. Studtard. Publ. Butterworth Heinemann, Boston (1995). Generally, glycopeptide compounds are differentiated by the placement of sugar substituents on the peptide core. In some instances differentiation arises from the positioning of fatty acid moieties on the sugar substituents. Research has shown that the sugar moieties attached to the core have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis*. M. Zmijewski & B. Briggs. "Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occured by a plurality of molecular mechanisms and that resistant organisms possess a diverse repertoire for counteracting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptide core molecules has been met by the present invention. Described herein are gtfB genes isolated from *Amycolatopsis orientalis* strain A82846 encoding glycosyltransferase enzyme GtfB. The GtfB enzyme adds D-glucose or D-xylose moieties onto the B ring of aglycosylvancomycin and adds D-glucose onto teichoplanin glyopeptides.

BRIEF SUMMARY

The present invention is designed to meet the aforementioned need and provides, inter alia, the isolated gtfB gene and other nucleic acid molecules that encode the GtfB gene product from *Amycolatopsis orientalis*. The invention also provides the GtfB protein product of the *Amycolatopsis orientalis* gtfB gene, in substantially purified form.

Having the cloned gtfB gene of *Amycolatopsis orientalis* enables the production of recombinant GtfB protein from which can be made novel derivatives of glycopeptide compounds.

In one embodiment the present invention relates to an isolated DNA molecule encoding GtfB protein, said DNA molecule comprising the nucleotide sequence identified as SEQ ID NO. 1:

```
ATGCGTGTGC TGTTGGCGAC GTGTGGATCG CGCG-
   GAGATA CCGAACCGCT GGTGGCACTG 60

GCGGTTCGGG TGCGGGACCT CGGCGCGGAT GTGCG-
   GATGT GCGCACCGCC GGACTGCGCG 120

GAGCGGCTGG CCGAGGTAGG TGTGCCGCAT GTGC-
   CCGTCG GCCCGTCGGC GCGCGCGCCG 180

ATCCAGCGAG CGAAACCGTT GACGGCCGAG GACGT-
   GCGCC GGTTCACGAC CGAGGCGATC 240

GCTACGCAGT TCGACGAGAT CCCGGCGGCG
   GCCGAGGGGT GTGCCGCGGT GGTGACCACC 300

GGCCTGCTGG CCGCCGCGAT CGGCGTGCGG TCGGTG-
   GCCG AGAAGCTGGG CATCCCCTAC 360

TTCTATGCCT TCCACTGTCC GAGTTATGTG CCGTCGCCGT
   ACTATCCGCC GCCGCCCCTC 420

GGCGAACCGT CCACACAGGA CACGATCGAC ATTCCG-
```

GCGC AGTGGGAGCG GAACAACCAG 480

AGCGCCTACC AGCGGTACGG CGGCCTGCTC AACAGC-
CACC GGGACGCGAT CGGCCTGCCA 540

CCGGTGGAGG ACATCTTCAC CTTCGGCTAC ACCGAT-
CACC CCTGGGTGGC GGCGGATCCG 600

GTGCTGGCCC CGCTGCAGCC GACAGACCTC GACGC-
CGTGC AGACCGGCGC GTGGATCCTG 660

CCCGACGAAC GGCCGCTTTC CCCGGAGCTG GCG-
GCGTTTC TGGACGCCGG CCCACCGCCG 720

GTGTACCTGG GGTTCGGCAG CCTGGGCGCA CCTGCT-
GACG CGGTCCGGGT GGCCATCGAC 780

GCGATCCGTG CCCATGGCCG CCGGGTGATC CTTTC-
CCGTG GCTGGGCCGA TTTGGTCCTG 840

CCCGACGACG GTGCCGACTG CTTCGCGATC GGC-
GAAGTGA ACCATCAGGT GCTGTTCGGC 900

CGAGTCGCCG CCGTCATCCA CCACGGCGGC
GCGGGCACGA CGCACGTGGC CGCGCGGGCA 960

GGTGCACCCC AGATCCTGTT GCCCCAGATG GCGGAC-
CAGC CGTACTACGC CGGCCGGGTG 1020

GCCGAACTGG GTGTTGGTGT GGCACATGAT GGTC-
CAATTC CGACCTTCGA TTCCTTGTCG 1080

GCCGCGCTTG CCACGGCTCT GACCCCCGAA
ACCCACGCGC GAGCGACGGC CGTGGCAGGC 1140

ACGATCCGCA CCGACGGGGC AGCGGTGGCC GCGCGGT-
TGC TGCTCGACGC GGTCAGTCGG 1200

GAAAAGCCGA CTGTTTCCGC G 1221

In another embodiment the present invention relates to a glycosyltransferase protein molecule, encoded by SEQ ID NO:1 wherein said glycosyltransferase protein molecule comprises the sequence identified as SEQ ID NO. 2.

In a further embodiment the present invention relates to a ribonucleic acid molecule encoding GtfB protein, said ribonucleic acid molecule comprising the sequence identified as SEQ ID NO. 3:

In yet another embodiment, the present invention relates to a recombinant DNA vector which incorporates the *Amycolatopsis orientalis* gtfB gene in operable linkage to gene expression sequences enabling the gtfB gene to be transcribed and translated in a host cell.

In still another embodiment the present invention relates to homologous or heterologous host cells which have been transformed or transfected with the cloned gtfB gene of *Amycolatopsis orientalis* such that the gtfB gene is expressed in the host cell.

In still another embodiment the present invention relates to a method for producing glycopeptide compounds wherein recombinantly produced GtfB protein is utilized to add one or more sugar moieties onto a glycopeptide core, in vitro.

In a further embodiment, the present invention relates to novel glycopeptide derivatives wherein xylose is added at the hydroxyl group of the B ring of aglycosylvancomycin or wherein glucose is added to the teichoplanin-related compound A47934.

DEFINITIONS

"A47934" refers to a glycopeptide compound, comprising a teichoplanin core said compound naturally lacking a sugar moiety. This and other related compounds are produced in *Streptomyces toyocaensis*.

"AGV," which denotes aglycosylvancomycin, comprises a vancomycin core having a free hydroxyl group on the B ring in place of the disaccharide moiety.

"DVV" denotes desvancosaminyl vancomycin in which a glucose residue is attached onto AGV at the free hydroxyl position of the B ring.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids, or a mix of aromatic and aliphatic amino acids.

"Glycosylating substrate" refers to a compound which functions as a donor of a sugar moiety in an enzymatic glycosylation reaction, for example, uridine diphosphate-D-glucose.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfB gene of *Amycolatopsis orientalis* A82846 encodes a glycosylating enzyme, GtfB. The enzyme will add D-glucose or D-xylose onto the free hydroxyl group of the B ring of aglycosylvancomycin (AGV), producing desvancosaminylvancomycin (DVV), or the xylose derivative thereof. The enzyme uses TDP-glucose, UDP-glucose, or UDP-xylose as the glycosylating substrate. The cloned GtfB enzyme will also add D-glucose onto a teichoplanin core. (see Table).

TABLE

| Glycosylating Substrate | AGV | Glycosylation Product Teichoplanin |
|---|---|---|
| No sugar | − | − |
| TDP-glucose | + | + |
| UDP-glucose | + | + |
| UDP-galactose | − | |
| UDP-mannose | − | |
| UDP-xylose | + | |
| UDP-N-acetylglucosamine | − | |
| UDP-galacturonic acid | − | |

The gtfB gene of *Amycolatopsis orientalis* comprises a DNA sequence of 1221 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention.

Gene Isolation Procedures

Those skilled in the art will recogize that the gtfB gene may be obtained by a plurality of applicable techniques including, for example, polymerase chain reaction (PCR) amplification, or de novo DNA synthesis. (See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the gtfB gene of *Amycolatopsis orientalis* or fragment thereof could also be isolated by PCR amplification of *Amycolatopsis orientalis* A82846 genomic DNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990), which hereby is incorporated by reference. The PCR amplification, which comprises genomic DNA, suitable enzymes, primers, and buffers, is conveniently carried out in a DNA Thermal Cycler (Perkin Elmer Cetus, Norwalk, Conn.). A positive PCR amplification is determined by detecting an appropriately-sized DNA fragment following agarose gel electrophoresis.

Protein Production Methods

One embodiment of the present invention relates to the substantially purified protein GtfB identified as SEQ ID NO:2 and encoded by the gtfB gene or functionally related proteins of *Amycolatopsis orientalis*.

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20_C. for thirty minutes followed by thirty minutes at 0_C.

The proteins of the present invention can also be produced by recombinant DNA methods using the cloned gtfB gene of *Amycolatopsis orientalis*. Recombinant methods are preferred if a high yield is desired. Expression of the cloned gtfB gene can be carried out in a variety of suitable host cells well known to those skilled in the art. The gtfB gene is introduced into a host cell by any suitable transformation, transfection, or conjugation means, well known to those skilled in the art. While chromosomal integration of the cloned gtfB gene is within the scope of the present invention, it is preferred that the gene be cloned into a suitable extra-chromosomally maintained expression vector so that the coding region of the gtfB gene is operably linked to a constitutive or inducible promoter.

The basic steps in the recombinant production of the GtfB protein are:

a) constructing a natural, synthetic or semi-synthetic DNA encoding GtfB protein;
b) integrating said DNA into an expression vector in a manner suitable for expressing the GtfB protein, either alone or as a fusion protein;
c) transforming, transfecting, or otherwise introducing said expression vector into an appropriate eukaryotic or prokaryotic host cell to form a recombinant host cell,
d) culturing said recombinant host cell under conditions that favor expression of the GtfB protein; and
e) recovering and purifying the GtfB protein by any suitable means.

Expressing Recombinant GtfB Protein in Procaryotic and Eucaryotic Host Cells

In general, prokaryotes are used for cloning DNA and for constructing the vectors of the present invention. Prokaryotes are also employed in the production of the GtfB protein. For example, the *Escherichia coli* K12 strain 294 (ATCC No. 31446) is particularly useful for the expression of foreign proteins. Other strains of *E. coli*, bacilli such as *Bacillus subtilis*, enterobacteriaceae such as *Salmonella typhimurium* or *Serratia marcescans*, various Pseudomonas species, and other bacteria, such as Streptomyces, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized by recombinant or chemical means as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to prokaryotes, mammalian host cells and eukaryotic microbes such as yeast may also be used to isolate and express the genes of the present invention. The simple eucaryote *Saccharomyces cerevisiae,* is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced GtfB Protein

An expression vector carrying the cloned gtfB gene of *Amycolatopsis orientalis* is transformed, transfected, or otherwise introduced into a suitable host cell using standard methods. Cells which contain the vector are propagated under conditions suitable for expression of the Glycosyltransferase protein. If the gtfB gene is under the control of an inducible promoter, growth media and other conditions should incorporate the appropriate inducer.

The recombinantly produced protein may be purified from cellular extracts of transformed cells by any suitable means. In a preferred protein purification method, the gtfB gene is modified at the 5' end to incorporate several histidine residues at the amino terminus of the GtfB protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in *Protein Purification: From Molecular Mechanisms to Large Scale Processes,* American Chemical Society, Washington, D.C. (1990), and in U.S. Pat. No. 4,569,794 both of which hereby are incorporated by reference. The IMAC method enables rapid isolation of substantially pure protein.

The gtfB gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the gtfB gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment thereof, and which is at least 15 base pairs in length, and which will selectively hybridize to *Amycolatopsis orientalis* DNA or mRNA encoding gtfB, is provided. Preferably, the 15 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1. Plasmid pCZA318 is an especially preferred DNA vector of the present invention.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pCZA318, which comprises SEQ ID NO:1. (See FIG. 1). Transformed host cells may be cultured under conditions well known to skilled artisans such that SEQ ID NO:2 is expressed, thereby producing GtfB protein in the recombinant host cell.

The cloned GtfB enzyme is useful for developing new glycopeptide compounds and for glycosylating already existing glycopeptide compounds in vitro. A method embodied herein comprises glycosylating a glycopeptide compound, by contacting the glycopeptide with the cloned GtfB protein and monitoring the glycopeptide compound that is produced.

In Vitro Glycosylation of Glycopeptides

The instant invention provides an enzymatic method for glycosylating vancomycin and teichoplanin core compounds in vitro using the cloned *A. orientalis* gtfB gene, said method comprising the steps of:

a) expressing the cloned gtfB gene in a host cell so that GtfB enzyme is produced;

b) exposing said GtfB enzyme to a glycopeptide compound, in vitro;

c) introducing a suitable glycosylating substrate; and d) characterizing and/or purifying the product glycopeptide by any suitable means.

The instant method can be used to enzymatically attach sugar residues to glycopeptide molecules such as, for example, AGV and teichoplanin core A47934. The method will, for example, attach a D-glucose or D-xylose moiety at the free hydroxyl group of the B ring of aglycosylvancomycin. The method can also be used to glucosylate teichoplanin derivatives that naturally lack sugar residues, such as, for example, compounds A41030A and A47934 (See e.g. M. Zmijewski and J. Fayerman. "Glycopeptide Antibiotics," In *Genetics and Biochemistry of Antibiotic Production,* Chap. 18. Ed. L. C. Vining and C. Studtard. Publ. Butterworth Heinemann, Boston (1995)).

The method can be adapted to substantially purified recombinant GtfB protein, as described herein, or to a crude cellular extract isolated from a recombinant cell culture that expresses the GtfB protein by virtue of having been transformed, transfected, or otherwise provided with the gtfB gene.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Amycolatopsis orientalis* Gene gtfB in *Escherichia coli*

Plasmid pCZA318 (see FIG. 1) is an approximately 6.9 kilobasepair expression vector suitable for expressing the gtfB gene at high levels in a procaryotic host, for example *E. coli*. Plasmid pCZA318 was derived from parent plasmid PET-11a (obtained from Novagen, Madison, Wis.), which contains an origin of DNA replication (ori), an ampicillin resistance gene (Amp), the T7 promoter region, and the lacI gene for repressing the lac operon.

The gtfB gene cassette inserted into pCZA318 was generated by the PCR carried out on *A. orientalis* A82846 genomic DNA using standard conditions. Primers used in the amplification reaction were complementary to the 5' and 3' ends of the gtfB gene sequence specified in SEQ ID NO: 1 and were engineered to contain NdeI and BglII restriction sites. The PCR-amplified gtfB gene sequence was digested with NdeI and BglII and ligated into pET11a, which had been digested with NdeI and BamHI.

EXAMPLE 2

Transformation of *Escherichia coli* with an Expression Plasmid Carrying the gtfB gene of *Amycolatopsis orientalis*

Plasmid pCZA318 was transformed into *E. coli* BL21 (DE3) (hsdS gal λcIts857 ind1Sam7nin5lacUV5-T7gene 1) using standard methods (See e.g. Sambrook et al. Supra).

EXAMPLE 3

In Vitro Glycosylation of Aglycosylvancomycin Using Cloned gtfB Gene

Approximately 25 ml of a culture of *E. coli* BL21(DE3) cells transformed with plasmid pCZA318 were grown to an $OD_{600}$ of about 0.6. Induction of gtfB gene expression was effected by adding 1 mM IPTG with shaking at room temperature for 2 to 3 hours. Thereafter, cells from about 20 ml of the induced culture were pelleted by centrifugation and resuspended in 2 ml of 50 mM Tris pH 9.0, 100 μg/ml lysozyme with incubation on ice for 10 minutes to effect cell lysis. After cell lysis the suspension was passed through a 23-gauge syringe and centrifuged at 10,000×g for 15 minutes to pellet cell debris. The resulting cell extract was used for the glycosylation reaction.

The 1 ml glycosylation reaction contained:
 1 mg AGV in 50 mM Tris HCL, pH 9.0
 5 mg TDP-glucose
 1 mg bovine serum albumin (BSA)
 20 μl 1M MgCl2
 20 μl 1M CaCl2
 5 μl 1M dithiothreitol (DTT)
 445 μl cell extract
 Distilled water to 1 ml.

A control reaction contained cell extract from non-transformed BL21(DE3). After incubation overnight at 37_C. with slight shaking the reaction was filtered through a 0.45 micron filter and analyzed by HPLC. The test sample but not the control showed a new peak appearing at about 10 minutes retention time, which peak was found by mass spectrometry to possess the mass expected of desvancosaminyl vancomycin.

EXAMPLE 4

In vitro Glycosylation of A47934 Using Cloned gtfB Gene

Cell extracts from recombinant cells harboring pCZA318 were prepared as in Example 3. The 1 ml glycosylation reaction contained:
 1 mg A47934
 5 mg TDP-xylose
 1 mg bovine serum albumin (BSA)
 20 μl 1M MgCl2
 20 μl 1M CaCl2
 5 μl 1M dithiothreitol (DTT)
 445 μl cell extract
 Distilled water to 1 ml.

A control reaction contained cell extract from non-transformed BL21(DE3). After incubation overnight at 37_C. with slight shaking the reaction was filtered through a 0.45 micron filter and analyzed by HPLC.

---

We claim:

1. An isolated nucleic acid compound encoding the protein having the amino acid sequence which is SEQ ID NO 2.

2. An isolated nucleic acid compound comprising a sequence encoding the protein of SEQ ID NO:2 where said compound has a sequence selected from the group consisting of:

(a)

ATGCGTGTGC TGTTGGCGAC GTGTGGATCG CGCG-
    GAGATA CCGAACCGCT GGTGGCACTG 60

GCGGTTCGGG TGCGGGACCT CGGCGCGGAT GTGCG-
    GATGT GCGCACCGCC GGACTGCGCG 120

GAGCGGCTGG CCGAGGTAGG TGTGCCGCAT GTGC-
    CGTCG GCCCGTCGGC GCGCGCGCCG 180

ATCCAGCGAG CGAAACCGTT GACGGCCGAG GACGT-
    GCGCC GGTTCACGAC CGAGGCGATC 240

GCTACGCAGT TCGACGAGAT CCCGGCGGCG
    GCCGAGGGGT GTGCCGCGGT GGTGACCACC 300

GGCCTGCTGG CCGCCGCGAT CGGCGTGCGG TCGGTG-
    GCCG AGAAGCTGGG CATCCCCTAC 360

TTCTATGCCT TCCACTGTCC GAGTTATGTG CCGTCGCCGT
    ACTATCCGCC GCCGCCCCTC 420

GGCGAACCGT CCACACAGGA CACGATCGAC ATTCCG-
    GCGC AGTGGGAGCG GAACAACCAG 480

AGCGCCTACC AGCGGTACGG CGGCCTGCTC AACAGC-
    CACC GGGACGCGAT CGGCCTGCCA 540

CCGGTGGAGG ACATCTTCAC CTTCGGCTAC ACCGAT-
    CACC CCTGGGTGGC GGCGGATCCG 600

GTGCTGGCCC CGCTGCAGCC GACAGACCTC GACGC-
    CGTGC AGACCGGCGC GTGGATCCTG 660

CCCGACGAAC GGCCGCTTTC CCCGGAGCTG GCG-
    GCGTTTC TGGACGCCGG CCCACCGCCG 720

GTGTACCTGG GGTTCGGCAG CCTGGGCGCA CCTGCT-
    GACG CGGTCCGGGT GGCCATCGAC 780

GCGATCCGTG CCCATGGCCG CCGGGTGATC CTTTC-
    CCGTG GCTGGGCCGA TTTGGTCCTG 840

CCCGACGACG GTGCCGACTG CTTCGCGATC GGC-
    GAAGTGA ACCATCAGGT GCTGTTCGGC 900

CGAGTCGCCG CCGTCATCCA CCACGGCGGC
    GCGGGCACGA CGCACGTGGC CGCGCGGGCA 960

GGTGCACCCC AGATCCTGTT GCCCCAGATG GCGGAC-
    CAGC CGTACTACGC CGGCCGGGTG 1020

GCCGAACTGG GTGTTGGTGT GGCACATGAT GGTC-
    CAATTC CGACCTTCGA TTCCTTGTCG 1080

GCCGCGCTTG CCACGGCTCT GACCCCCGAA
    ACCCACGCGC GAGCGACGGC CGTGGCAGGC 1140

ACGATCCGCA CCGACGGGGC AGCGGTGGCC GCGCGGT-

TGC TGCTCGACGC GGTCAGTCGG 1200

GAAAAGCCGA CTGTTTCCGC G 1221 which is SEQ ID NO:1;

(b)

AUGCGUGUGC UGUUGGCGAC GUGUGGAUCG CGCG-
    GAGAUA CCGAACCGCU GGUGGCACUG 60

GCGGUUCGGG UGCGGGACCU CGGCGCGGAU GUGCG-
    GAUGU GCGCACCGCC GGACUGCGCG 120

GAGCGGCUGG CCGAGGUAGG UGUGCCGCAU GUGC-
    CGUCG GCCCGUCGGC GCGCGCGCCG 180

AUCCAGCGAG CGAAACCGUU GACGGCCGAG
    GACGUGCGCC GGUUCACGAC CGAGGCGAUC 240

GCUACGCAGU UCGACGAGAU CCCGGCGGCG
    GCCGAGGGGU GUGCCGCGGU GGUGACCACC 300

GGCCUGCUGG CCGCCGCGAU CGGCGUGCGG UCGGUG-
    GCCG AGAAGCUGGG CAUCCCCUAC 360

UUCUAUGCCU UCCACUGUCC GAGUUAUGUG CCGUCGC-
    CGU ACUAUCCGCC GCCGCCCCUC 420

GGCGAACCGU CCACACAGGA CACGAUCGAC AUUCCG-
    GCGC AGUGGGAGCG GAACAACCAG 480

AGCGCCUACC AGCGGUACGG CGGCCUGCUC AACAGC-
    CACC GGGACGCGAU CGGCCUGCCA 540

CCGGUGGAGG ACAUCUUCAC CUUCGGCUAC
    ACCGAUCACC CCUGGGUGGC GGCGGAUCCG 600

GUGCUGGCCC CGCUGCAGCC GACAGACCUC GACGC-
    CGUGC AGACCGGCGC GUGGAUCCUG 660

CCCGACGAAC GGCCGCUUUC CCCGGAGCUG GCGGCGU-
    UUC UGGACGCCGG CCCACCGCCG 720

GUGUACCUGG GGUUCGGCAG CCUGGGCGCA
    CCUGCUGACG CGGUCCGGGU GGCCAUCGAC 780

GCGAUCCGUG CCCAUGGCCG CCGGGUGAUC CUUUC-
    CCGUG GCUGGGCCGA UUUGGUCCUG 840

CCCGACGACG GUGCCGACUG CUUCGCGAUC GGC-
    GAAGUGA ACCAUCAGGU GCUGUUCGGC 900

CGAGUCGCCG CCGUCAUCCA CCACGGCGGC
    GCGGGCACGA CGCACGUGGC CGCGCGGGCA 960

GGUGCACCCC AGAUCCUGUU GCCCCAGAUG GCGGAC-
    CAGC CGUACUACGC CGGCCGGGUG 1020

GCCGAACUGG GUGUUGGUGU GGCACAUGAU GGUC-
    CAAUUC CGACCUUCGA UUCCUUGUCG 1080

GCCGCGCUUG CCACGGCUCU GACCCCCGAA
    ACCCACGCGC GAGCGACGGC CGUGGCAGGC 1140

ACGAUCCGCA CCGACGGGGC AGCGGUGGCC GCGCGG-
    UUGC UGCUCGACGC GGUCAGUCGG 1200

GAAAAGCCGA CUGUUUCCGC G 1221 which is SEQ ID NO:3;

(c) a nucleic acid compound complementary to (a) or (b).

3. An isolated nucleic acid compound of claim 2 wherein the sequence of said compound is SEQ ID NO:1 or a sequence complementary to SEQ ID NO:1.

4. An isolated nucleic acid compound of claim 2 wherein the sequence of said compound is SEQ ID NO:3 or a sequence complementary to SEQ ID NO:3.

5. A vector comprising an isolated nucleic acid compound of claim 2.

6. A vector, as in claim 5, wherein said isolated nucleic acid compound is DNA operably linked to a promoter sequence.

7. A host cell containing the vector of claim 5.

8. A host cell containing the vector of claim 6.

9. A method for constructing a recombinant host cell having the potential to express SEQ ID NO:2, said method comprising introducing into said host cell by any suitable means a vector of claim 6.

10. A method for expressing SEQ ID NO:2 in the recombinant host cell of claim 9, said method comprising culturing said recombinant host cell under conditions suitable for gene expression.

* * * * *